(12) United States Patent  (10) Patent No.: US 7,731,423 B2
Caminade et al.  (45) Date of Patent: Jun. 8, 2010

(54) MATTRESS COVER APPARATUS HAVING X-RAY CASSETTE RECEPTACLE AND METHOD

(75) Inventors: Jean-Luc Caminade, Saint Jean de Vedas (FR); Thierry Flocard, Montpellier (FR)

(73) Assignee: Hill-Rom Industries S.A., Montpellier (FR)

( * ) Notice: Subject to any disclaimer, the term of this patent is extended or adjusted under 35 U.S.C. 154(b) by 0 days.

(21) Appl. No.: 11/876,000

(22) Filed: Oct. 22, 2007

(65) Prior Publication Data

US 2008/0095322 A1   Apr. 24, 2008

(30) Foreign Application Priority Data

Oct. 23, 2006  (FR)  .................................. 06 54447

(51) Int. Cl.
*G03B 42/02*  (2006.01)

(52) U.S. Cl. ........................................ 378/177; 378/178

(58) Field of Classification Search ................. 378/167, 378/177, 178, 180, 181; 5/601
See application file for complete search history.

(56) References Cited

U.S. PATENT DOCUMENTS

| 3,551,923 | A | 1/1971 | Franklin |
| 4,156,145 | A | 5/1979 | Weatherholt |
| 4,665,574 | A | 5/1987 | Filips et al. |
| 4,893,323 | A | 1/1990 | Cook, III |
| 5,016,268 | A | 5/1991 | Lotman |
| 6,398,409 | B1 | 6/2002 | Brooks |
| 6,652,140 | B1 | 11/2003 | Taber et al. |
| 6,893,156 | B2 | 5/2005 | Sharpensteen et al. |
| 2003/0115672 | A1* | 6/2003 | Newkirk ........................ 5/600 |

* cited by examiner

*Primary Examiner*—Jurie Yun
(74) *Attorney, Agent, or Firm*—Barnes & Thornburg LLP

(57) ABSTRACT

A protective cover for a cushion or mattress is disclosed. The protective cover has an upper part, an internal pocket to contain a radiography cassette, and an inflatable support element between the internal pocket and the upper part.

12 Claims, 3 Drawing Sheets

MATTRESS COVER APPARATUS HAVING X-RAY CASSETTE RECEPTACLE AND METHOD

The present application claims priority, under 35 U.S.C. §119(a), of French National Application No. 06 54447 which was filed Oct. 23, 2006 and which is hereby incorporated by reference herein.

BACKGROUND

The present disclosure relates to a process and radiography device by means of a radiography cassette adapted on a support element, of cushion or mattress type arranged respectively on a seat or bed, on which rests a part at least of the body of the patient, allowing said patient resting on said support element to be radiographed.

A radiography cassette is classically made up of a plate with a rigid, thin parallelepiped square, such as a metal or synthetic square incorporating a photosensitive support for a type of radiation employed, especially and most generally, X-rays.

A process consisting of lifting the patient and placing the radiography cassette directly under the part of the body of the patient to be radiographed between the body of the patient and the face of the support element supporting the part of the body to be radiographed, especially the upper face of the support element in the case of a mattress on a bed is known.

This process is barely practical, since it requires the patient to be lifted and causes disturbance to the patient by a number of handlers. Also, in the case of strongly traumatized patients, this type of handling is proscribed, as any handling of the patient constitutes a risk for his integrity, especially in the case of fractures of the spine or severe burns.

A process is also known in which the radiography cassette cooperates with a cassette support integral with the bed or seat frame, in fact below or behind the latter, which is then covered by said support element of cushion or mattress type for the purpose of comfort of the patient whose part of the body to be radiographed rests on said support element.

This process is less disturbing for the patient, but does pose a problem of image quality obtained by radiography, in light of moving the zones away from the body to be radiographed, as much as the height of the frame and thickness of the support element.

A disadvantage of this process in particular is that the equipment arranged between the cassette and the body to be radiographed can generate artifacts.

SUMMARY

Devices according to this disclosure provide an improved process and device for radiographing, using a cassette, a part at least of the body of a patient resting on a support element of the body, such as a cushion or mattress, arranged respectively on a seat or a bed, allowing the part of the body of the patient to be radiographed as closely as possible, while keeping the patient uninjured, that is, with maximum limitation of any handling of the patient and with maximum comfort for the latter during handling, then during radiography following introduction of the cassette.

Devices according to this disclosure provide a process and device simpler to use and higher performing, especially in terms of decreasing risks of injury to the patient and improvement of the radiographic quality and thus provide a process and device facilitating handling for introduction and withdrawal of the cassette.

One device according to this disclosure provide a protective cover of a main support element of cushion or mattress type, on which a part at least of the body of a patient to be radiographed is intended to rest, said cover comprising at least an upper part substantially flat when placed so as to cover the upper surface of said main support element and lateral flanges, for covering in part at least the flanks of the main support element, characterised in that it comprises: a supple internal pocket, extending below said upper part of the cover, for holding a radiography cassette, said pocket comprising at least one opening for introducing a cassette, the end of the pocket forming an opening terminating on and being fixed to at least one lateral edge of the cover, near the longitudinal edge of said main cover part, and a secondary support element of mattress or cushion type, not as thick as said main support element, in some instances, having a thickness of less than 5 cm, integral with said cover, positioned in between said pocket and said upper cover part and covering at least said pocket.

Using said secondary support element on the one hand protects the patient during introduction of said cassette into said pocket and during radiography and, on the other hand, facilitates introduction handling of said cassette by a single operator, at the same time eliminating the natural surface deformations of the physical body, which are particularly accentuated in the case of emaciated patients whose spines protrude, or even in the case of spastic patients.

The pocket contributes to protecting the main and secondary support elements during handling of the cassette in contact with the latter for introduction and withdrawal of the cassette, and facilitates placing of the cassette, specifically its guiding, and are held in the correct position, between the cover and the main support element.

Said main support element and said secondary support element are, in some embodiments, constituted by cells in the shape of transversally arranged beads filled with fluid, preferably air, the cells of said secondary support element having a cross-section reduced relative to that of said main support element, and it is contemplated that said section reduced being larger in size, such as a diameter of less than 5 cm.

Also according to this disclosure, the cells of said main support element and secondary support element are filled with air and are connected to a pressure-regulating device inside said cells, as a function of the lift of the patient at different zones of the body of the patient, the pressure inside the cells of said secondary support element being substantially identical to that of the cells of the zone of said main support element opposite to it.

These mattresses constituted by cells in the shape of beads or transversal cylinders inflated by air have therapeutic viewing, especially in the prevention of bedsores.

In fact, they commonly regulate the buoyancy of patients by varying and regulating the air pressure of the different cells in the different zones of the mattress according to their localization to obtain optimal distribution of the interface pressure between the body and the mattress, which, if desired, regulates the pressure of said secondary support element and of said main support element, especially of the zone of the main support element located opposite said secondary support element on one hand, to facilitate introduction and evacuation of the radiography cassette, and also to continue regulation of the interface pressure, especially for homogenizing the interface pressure between the patient and said mattress during radiography.

In some embodiments, said pocket is constituted by a fine synthetic fabric having mechanical resistance properties to tearing and a high glide coefficient. In fact, when the radiography cassette is pushed into the pocket it neither needs to be braked by adherence of the fabric on its internal face in said pocket, nor do the parts of the cassette projecting at angles have to risk tearing the fabric.

For example, said pocket is constituted by a synthetic fabric of a gram size less than 100 g/m2, is hot-calendered and has at least one face corresponding to the internal face of the pocket covered by a layer of polymer resin, such as a fluorinated polymer, imparting glide properties.

This type of hot-calendering crushes the synthetic surface threads and closes the mesh of the fabric, giving the material mechanical resistance properties to traction and high resistance to spreading of tears as well as a strong glide coefficient.

Fabrics of this type are utilized for fabricating parachute and sailboat spinnaker cloths.

More particularly, the pocket may be constituted by a fabric having resistance to traction of at least 20 daN, preferably at least 40 daN according to standard ISO 1393-1 test and resistance to spreading of tears of at least 10N, preferably at least 20N according to the ISO 13937-1 test.

This resistance test to traction signifies that the fabric resists traction up to 20 daN, preferably up to 40 daN and no longer tears when there is spreading of tears under the effect of traction of at least 10N, preferably at least 20N.

These mechanical resistance and glide properties of the fabric making up the pocket on the internal face of the pocket facilitate introduction or withdrawal operations of the cassette by a single operator without excessive disturbance to the patient to be radiographed.

In one embodiment, an upper part of the end of the pocket forming the opening is fixed at a longitudinal edge of said upper cover part, and the other lower part of the end of the pocket forming said opening is fixed at the top of said corresponding lateral edge of the cover.

In an embodiment, said pocket comprises two opposite openings, said pocket thus forming a sheath passing through the cover between the two opposite longitudinal edges and lateral flanges opposite said cover.

The sheath constitutes a sleeve for passage of the cassette or introduction of the cassette via any of the two openings.

Also, in the event of successive radiographies, this embodiment links the radiographies faster and more easily by a movement passing through a unidirectional line, by inserting the cassettes, for example, one after the other via the same opening and then evacuating them via the opposite opening, after radiography.

Said pocket opening is possibly equipped with a reversible opening/closing slide device, possibly protected by a lateral rebate integral with said cover.

This reversible opening/closing device and this rebate protect the interior of the cover from penetration by liquid and/or any pollution or contamination generated by the patient and/or any parasitic element risking generating artifacts on the radiography.

In some embodiments, the dimension of the pocket in the longitudinal direction of said main support element positions a cassette opposite a zone of said upper part of the cover on which is intended to rest a part of the body of the patient extending from the occiput to the pelvis of the patient, such as at a distance of ½ to ⅔ of the length of said cover from one of these ends in the longitudinal direction.

Also disclosed is a protective cover, characterised in that it covers a main support element of cushion or mattress type, such as arranged respectively on a seat or a bed.

Another aspect of the present disclosure is a radiography process of part at least of the body of a patient using a radiography cassette, at least the part of the body of the patient to be radiographed resting on a main support element of cushion or mattress type, characterised in that a cassette is inserted into a pocket of a protective cover according to this disclosure.

In some embodiments of the process according to the disclosure, a cover comprising a tubular pocket in the shape of a sheath with two openings terminating in and fixed on the opposite longitudinal edges and lateral flanges opposite a cover is used, and a cassette is introduced via a opening, radiography is performed and said cassette is evacuated via the opening opposite.

In some embodiments of the process according to the disclosure, the pressure inside said main support element and secondary support element constituted by cells in the shape of beads arranged transversally and filled with air is regulated so as to homogenize the interface pressure between the body of the patient and said support elements main and secondary, by maintaining pressure inside the cells of said secondary support element substantially identical to the cells in the zone of said main support element opposite said secondary support element.

BRIEF DESCRIPTION OF THE DRAWINGS

Other characteristics and advantages of the devices according to this disclosure will emerge from the following detailed description of an embodiment, done in reference to FIGS. 1 to 3, in which.

DETAILED DESCRIPTION OF THE DRAWINGS

Figure 1:
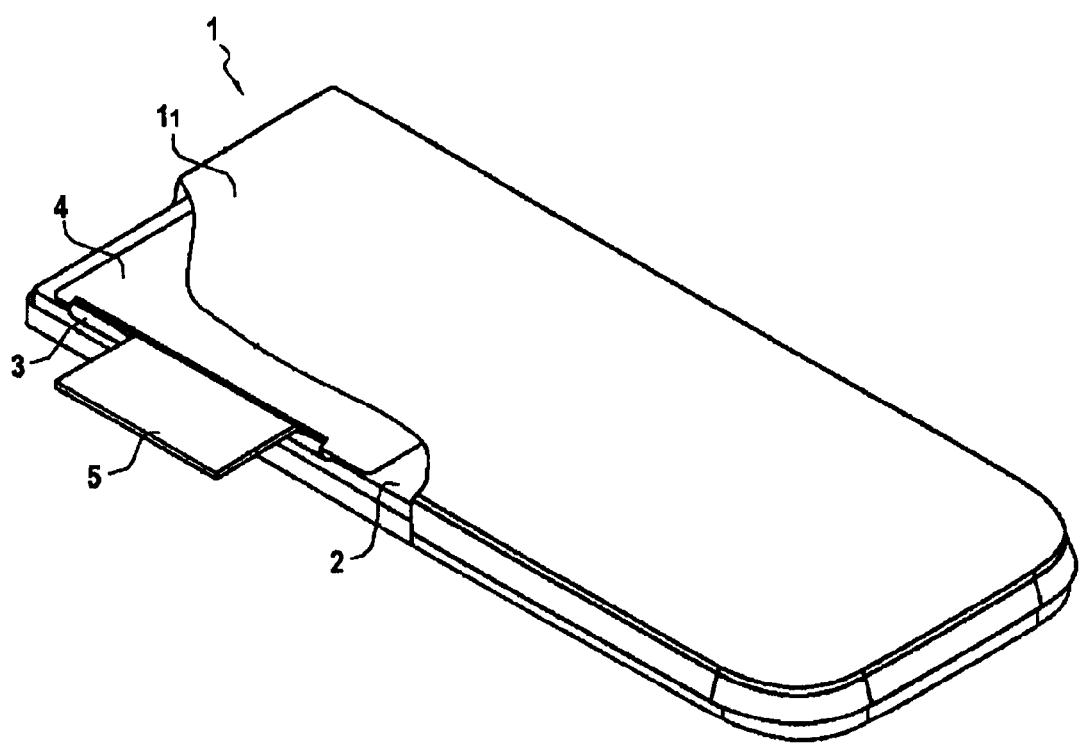
FIG. 1 illustrates an ensemble view, showing a protective cover 1 according to the disclosure covering a main mattress 2 with a radiography cassette 5 in the course of insertion into a pocket 3 according to the disclosure.
Figure 2:
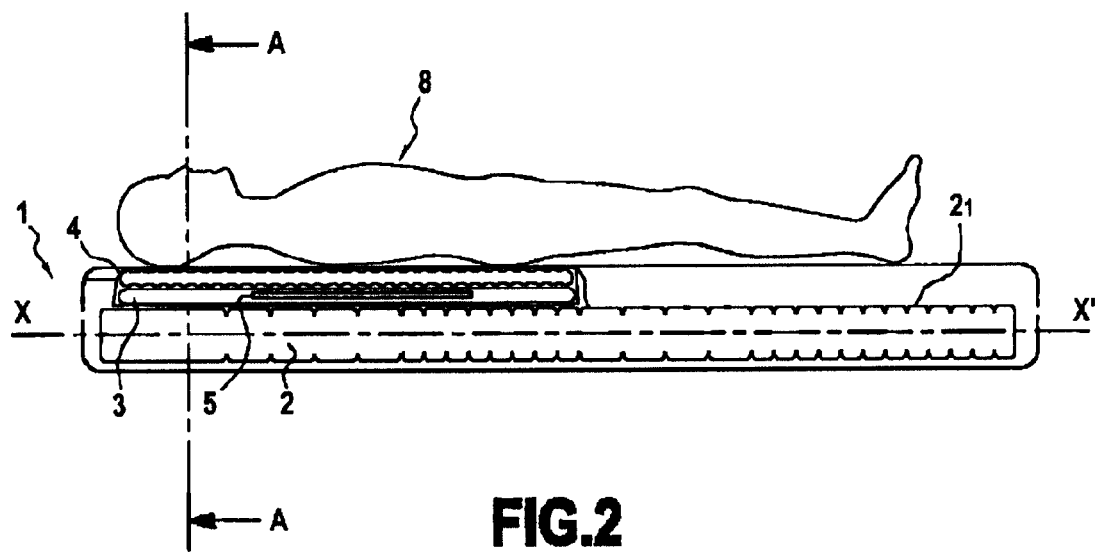
FIG. 2 is a view in longitudinal section of the ensemble according to FIG. 1 with a patient 8 stretched out on a cover according to the disclosure.
Figure 3:
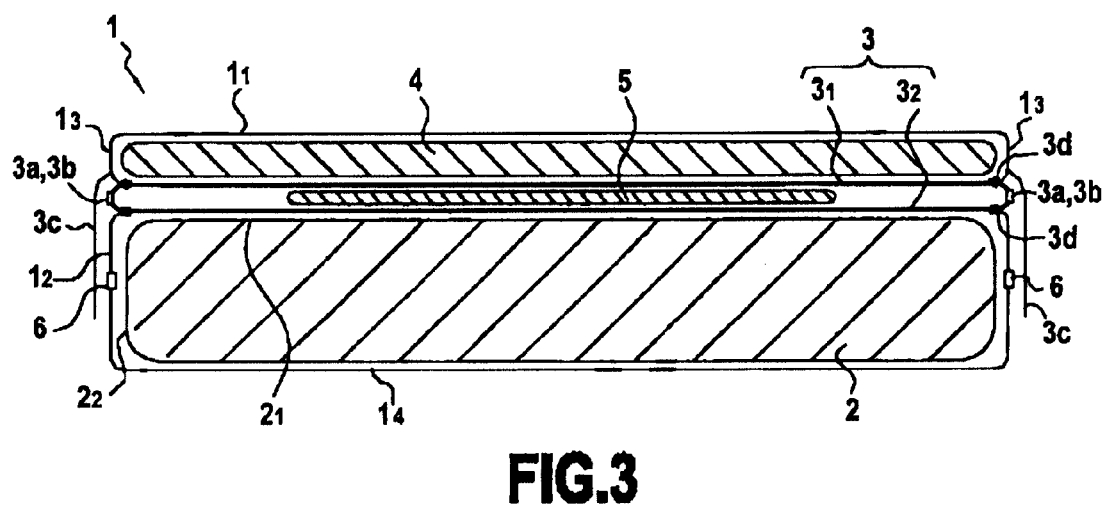
FIG. 3 is a view in transversal section according to AA of FIG. 2.

FIGS. 1 to 3 illustrate a protective cover 1 according to the disclosure, equipped with a pocket in the shape of a tubular sheath 3 with opposite openings 3a terminating on the two opposite lateral edges $1_2$ and longitudinal edges $1_3$ of the upper part $1_1$ opposite the protective cover.

The two openings 3a are equipped with opening/closing slide devices 3b covered by a protective rebate 3c.

The peripheral edge of each lateral opening 3a of the pocket 3 is fixed to the cover by seams 3d with a first seam between the peripheral edge of an upper part $3_1$ of the pocket 3 and a longitudinal edge $1_3$ of the upper part $1_1$ of the cover and, a second seam 3d between the peripheral edge of a lower part $3_2$ of the pocket and the upper end of the lateral edge $1_2$ of the cover covering the flanks $2_2$ of the support element or mattress.

FIG. 3 illustrates a second slide closing device 6 which follows the peripheral contour of the lateral edge $1_2$ of the cover, so that the mattress and the protective rebate 3c likewise protect this second opening/closing slide device 6.

This second opening/closing slide device 6 separates the upper part from the lateral flanges $1_2$ of the cover and a lower part $1_4$ of the cover.

The pocket 3 forms a sheath via which radiography cassettes 5 can be translated, from one opening to the other, when the opening/closing slide devices 3b are open.

The fabrics making up the upper part $1_1$ and the lateral flanges $1_2$ of the protective cover are synthetic fabrics of polyester or polyamide type coating on at least the external surface of the polyurethane polymer cover having sealing properties, inter alia.

The sheath is constituted by a polyamide textile material forming a fine fabric of 66 g/m² coating on one of its faces by a debeading fluorinated resin, and hot-calendered. This fabric exhibits resistance properties to traction and resistance of at least 45 daN according to ISO 13934-1 standard and resistance to spreading of tears according to ISO 13937-1 standard of at least 20N.

Due to its hot calendering and being covered by a layer of fluorinated resin, this cloth has increased glide properties.

A cloth of this type is marketed by the company JEANNE BLANCHIN at CHAMPAGNEUX, 73240—France under reference MELBOURNE 3380.

This type of supple and fine fabric is classically used for making sails of spinnaker type and parachute cloth.

Placed in between the pocket 3 and the upper part $1_1$ of the cover on which rests the patient to be radiographed is a cushion or secondary support element 4 formed according to the same structure as the main mattress 2 protected by said cover.

The different materials used in the cover, the pocket and the secondary support element 4 are transparent to rays used in radiography, especially X-rays.

In some embodiments, a main support element 2 or main mattress 2 constituted by beads $2_1$ arranged transversally and inflated by air, from 10 to 20 cm in thickness is employed.

The secondary support element 4 is likewise constituted by beads $4_1$ inflated by air and arranged transversally, though smaller in diameter (specifically around 3 cm) extending substantially over the entire width of the mattress 2 and, in the longitudinal direction X, X', over the entire length of the pocket and limited thereto.

The openings 3a of the sheath are slightly larger than the dimension of the standard large-format cassettes to be radiographed, specifically around 50 cm.

However, the pocket in some embodiments extends over a length of ½ to ⅔ of the length of the mattress in order to cover the zones of the part of the body to be radiographed able to extend from the occiput to the pelvis, irrespective of the morphology of the patient.

The secondary support element 4 is inflated prior to introduction and evacuation of the cassette by a single operator to the extent where handling the patient is much easier.

The radiography assays as conducted demonstrate a satisfactory radiographic quality devoid of any artefact and the possibility of introduction and withdrawal of the radiography cassette in the pocket by a single operator with minimal disturbance to the patient to be radiographed compatible in the case of polytraumatised patients.

In a known manner, the cells $2_1$, $4_1$ of the main support elements and secondary support elements 4 are connected by a network of tubes and valves $7_1$ to a pressure-regulating device 7 inside the cells constituting it, if needed, according to the different zones of the or of said mattress, and the air pressure in said cells is regulated so as to maintain the homogeneity of the interface pressure between the body of the patient and the mattress.

Figure 4:
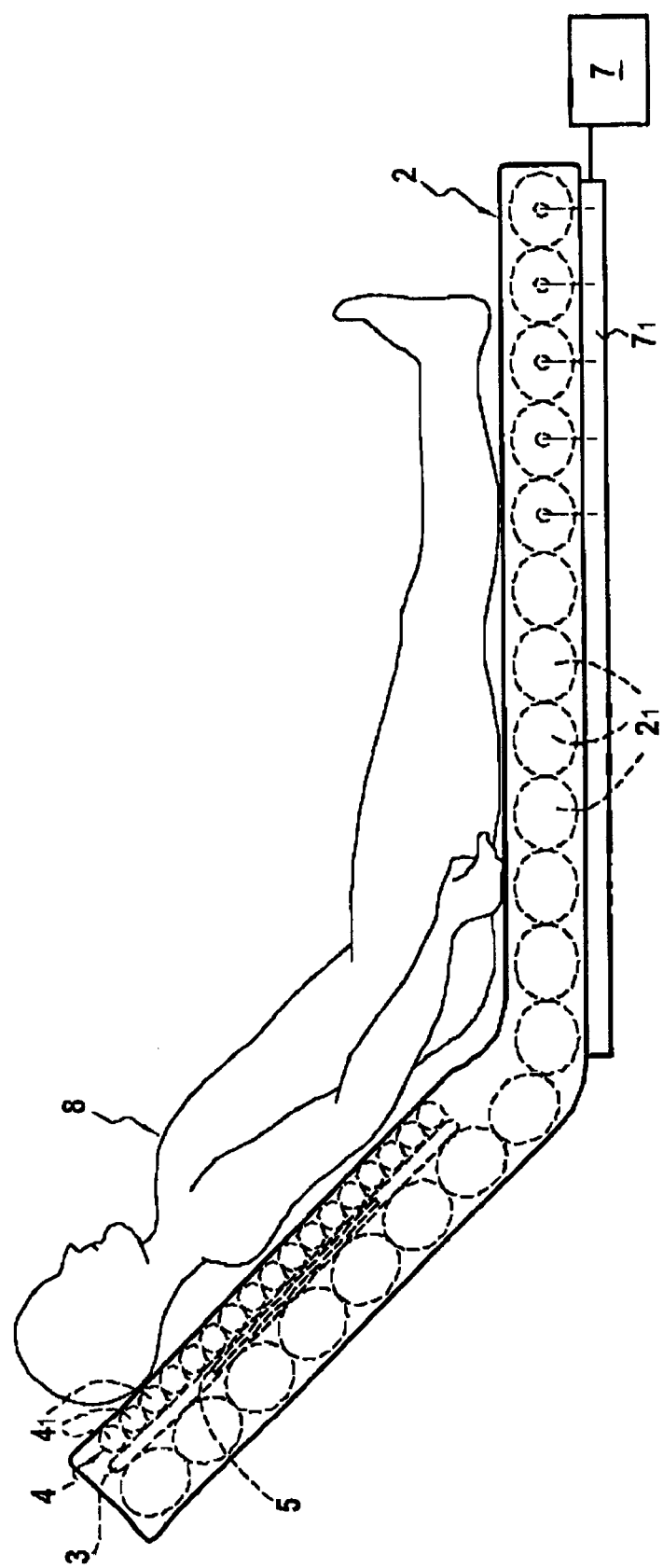
FIG. 4 is a view in transversal section of said main and secondary support elements constituted by beads lifted in inclination.

FIG. 4 illustrates part only of the network $7_1$ of valves and tubes connecting the regulating device 7 comprising a pump so as not to overload the diagram.

In some instances, the pressure in the cells of said secondary support element is substantially identical to that in the cells of said main support element located opposite said secondary support element.

Finally, as per FIG. 4, to avoid disturbing the patient 8 contacting an excess thickness of the mattress in the zone corresponding to said secondary support element, the top of the bed and the corresponding zone of the mattress are lifted and inclined at around 45°, so that the interface pressure between the body and the mattress is reduced in the zone of said secondary support element. It is thus possible to continue therapeutic regulation of the pressure inside the cells of said main and secondary support elements during radiography.

The invention claimed is:

1. A protection cover of a main support element of a cushion or a mattress type, on which at least a part of a body of a patient to be radiographed is intended to rest, said protection cover comprising
at least an upper part that is substantially flat when placed so as to cover an upper surface of said main support element,
an internal pocket extending underneath said upper part of the cover, the internal pocket being provided within a tubular sheath having an upper layer of material and a lower layer of material, the tubular sheath being fastened to the upper part, the internal pocket being suitable for containing a radiography cassette, said internal pocket comprising at least one opening in the tubular sheath for introducing the radiography cassette, the at least one opening being located adjacent at least one lateral edge of the cover near the a longitudinal edge of said upper part, the internal pocket extending over about half the overall length of the main support part such that the internal pocket is sufficiently larger than the radiography cassette to allow repositioning of the radiography cassette relative to the internal pocket, and
a secondary support element, not as thick as said main support element, integral with said cover, positioned between said internal pocket and said upper part and covering at least said internal pocket, wherein said secondary support element comprises inflatable cells that are filled with air, the cells of said secondary support element having a cross-section reduced relative to a cross-section of said main support element.

2. The protection cover as claimed in claim 1, wherein said reduced cross-section has a dimension of less than 5 cm.

3. The protection cover as claimed in claim 1, wherein the main support element has inflatable cells, the cells of said main support element and said secondary support element are connected to a regulating device that regulates the pressure inside said cells such that the pressure inside the cells of said secondary support element is substantially identical to that of the cells of the main support element.

4. The protection cover as claimed in claim 1, wherein said tubular sheath within which the internal pocket is provided is constituted by a fine synthetic fabric having high mechanical resistance properties to tearing and high glide coefficient.

5. The protection cover as claimed in claim 1, wherein the upper layer of material is fixed adjacent the at least one opening to the upper cover part and wherein the lower layer of material is fixed adjacent the at least one opening to the at least one lateral edge of the cover.

6. The protection cover as claimed in claim 1, wherein the at least one opening of said internal pocket comprises two opposite openings on opposite sides of said tubular sheath.

7. The protection cover as claimed in claim 1, wherein the dimension of the internal pocket in a longitudinal direction of said main support element permits positioning of the cassette with respect to the body of the patient resting on the main support element from the occiput to the pelvis of the patient, over a distance of ½ to ⅔ of the length of said protection cover in the longitudinal direction.

8. The protection cover as claimed in claim 1, wherein the protection cover covers at least a portion of the main support element when the main support element is arranged respectively on a seat or a bed.

9. A radiography process of at least part of the body of a patient by means of a radiography cassette, at least the part of the body of the patient to be radiographed resting on a main support element of cushion or mattress type, wherein the radiography cassette is inserted into a pocket of a protection cover as claimed in claim 8.

10. The process as claimed in claim 9, wherein the at least one opening in the tubular sheath comprises two openings and the cassette is introduced via one of the two openings such that after radiography is performed, said cassette is able to be evacuated via the other opening of the two openings.

11. The process as claimed in any one of claims 9 or 10, wherein the main support element comprises inflatable cells and a pressure inside said inflatable cells of said main support element and inside said inflatable cells of said secondary support element are regulated such that the pressure inside said inflatable cells of said secondary support element is substantially identical to the pressure inside said inflatable cells of said main support element.

12. A protection cover of a main support element of a cushion or a mattress type, on which at least a part of the body of a patient to be radiographed is intended to rest, said protection cover comprising at least an upper part that is substantially flat when placed so as to cover an upper surface of said main support element, an internal pocket extending underneath said upper part of the cover, the internal pocket being suitable for containing a radiography cassette, said internal pocket comprising at least one opening for introducing the radiography cassette, the at least one opening being located adjacent at least one lateral edge of the protection cover near the longitudinal edge of said upper part, and a secondary support element, not as thick as said main support element, integral with said cover, positioned between said internal pocket and said upper cover part and covering at least said internal pocket, wherein said pocket is constituted by a fine synthetic fabric having high mechanical resistance properties to tearing and high glide coefficient, wherein said synthetic fabric has a gram weight under 100 g/m$^2$, is hot-calendered and, whereof at least one internal face of said pocket is covered by a layer of fluorinated polymer resin which imparts glide properties.

* * * * *